United States Patent
Bertram et al.

(10) Patent No.: US 6,730,795 B2
(45) Date of Patent: *May 4, 2004

(54) PROCESS FOR THE PREPARATION OF PHENYLENE-BIS-BENZIMIDAZOLE-TETRASULFONIC ACID DISODIUM SALT

(75) Inventors: Ralf Bertram, Holzminden (DE); Stephan Hillers, Holzminden (DE); Oskar Koch, Göttingen (DE); Harry Erfurt, Uslar (DE); Gerald Reinders, Salzkotten (DE)

(73) Assignee: Symrise GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/995,328

(22) Filed: Nov. 27, 2001

(65) Prior Publication Data
US 2002/0082429 A1 Jun. 27, 2002

(30) Foreign Application Priority Data
Nov. 29, 2000 (DE) .......................................... 100 59 254

(51) Int. Cl.[7] ...................... C07D 403/10; C07C 309/00

(52) U.S. Cl. ...................................... 548/305.4; 562/30
(58) Field of Search .......................... 548/305.4; 562/30

(56) References Cited

U.S. PATENT DOCUMENTS

| | | | | |
|---|---|---|---|---|
| 2,463,264 A | | 3/1949 | Graenacher et al. | ........ 260/240 |
| 3,536,730 A | | 10/1970 | Baron et al. | ............. 260/309.2 |
| 5,473,079 A | * | 12/1995 | Heywang et al. | |
| 5,585,091 A | | 12/1996 | Pelzer et al. | .................. 424/60 |
| 6,214,324 B1 | | 4/2001 | Candau | ...................... 424/59 |

FOREIGN PATENT DOCUMENTS

DE      440 989      2/1927

OTHER PUBLICATIONS

Wang et al American Chemical Society, 220th National Meeting, Abstract POLY–416, 2000.*

* cited by examiner

Primary Examiner—Johann Richter
Assistant Examiner—Paul A. Zucker
(74) Attorney, Agent, or Firm—Pendorf & Cutliff

(57) ABSTRACT

Phenylene-bis-benzimidazole-tetrasulfonic acid disodium salt which is largely free from impurities can be prepared by reacting o-phenylenediamine with terephthalic acid and chlorosulfonic acid in the presence of strong acids with a reaction time of 10 to 15 hours.

7 Claims, No Drawings

PROCESS FOR THE PREPARATION OF PHENYLENE-BIS-BENZIMIDAZOLE-TETRASULFONIC ACID DISODIUM SALT

FIELD OF THE INVENTION

The present invention relates to a process for the preparation of the phenylene-bis-benzimidazole-tetrasulfonic acid disodium salt which is largely free from impurities.

BACKGROUND OF THE INVENTION

The preparation of the phenylene-bis-benzimidazole-tetrasulfonic acid disodium salt is known per se (DE A 440 96 89). The process can be explained by the following equation:

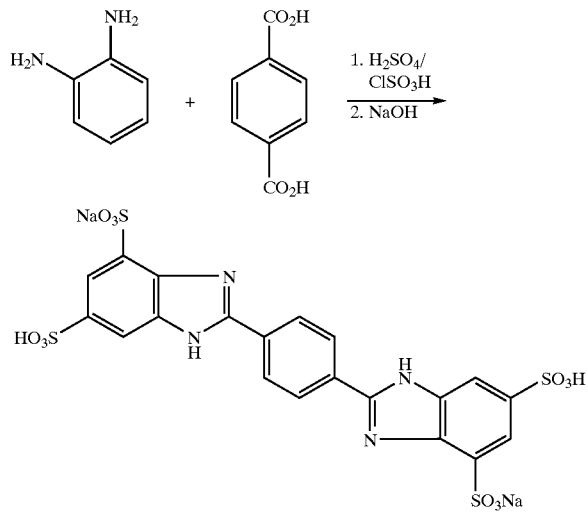

Phenylene-bis-benzimidazole-tetrasulfonic acid disodium salt is then carried out at a temperature of about 120° C. at a reaction time of one hour. Hydrolysis in ice water is then carried out, phenylene-bis-benzimidazole-tetrasulfonic acid disodium salt crystallizing out; the crystallizate is filtered off. The still moist crystallizate is then taken up and dissolved in an alkaline hydroxide solution, such as sodium hydroxide solution, then treated with activated carbon and heated. The activated carbon is filtered off, and the phenylene-bis-benzimidazole-tetrasulfonic acid disodium salt is precipitated out by adding sulfuric acid. Drying gives pulverulent phenylene-bis-benzimidazole-tetrasulfonic acid disodium salt with a purity of 99% by weight.

During the performance testing of the phenylene-bis-benzimidazole-tetrasulfonic acid disodium salt prepared in this way, it is found that the use of this product prepared in accordance with the above process leads to unacceptable discolorations in the formulations.

A cause of the discolorations are, inter alia, diphenylamine, 3,4-diamino-benzenesulfonic acid and 2-(4'-carboxy-phenyl)-benzimidazole-6-sulfonic acid.

SUMMARY OF THE INVENTION

An object of the present invention is the preparation of phenylene-bis-benzimidazole-tetrasulfonic acid disodium salt in high purity which, in particular, does not contain any discoloring components.

We have found a process for the preparation of phenylene-bis-benzimidazole-tetrasulfonic acid disodium salt by reacting o-phenylenediamine with terephthalic acid and chlorosulfonic acid in the presence of strong acids, which is characterized in that the reaction time is 10 to 15 hours.

DETAILED DESCRIPTION OF THE INVENTION

The process according to the present invention gives phenylene-bis-benzimidazole-tetrasulfonic acid disodium salt in a purity greater than 98% by weight. By-products are merely

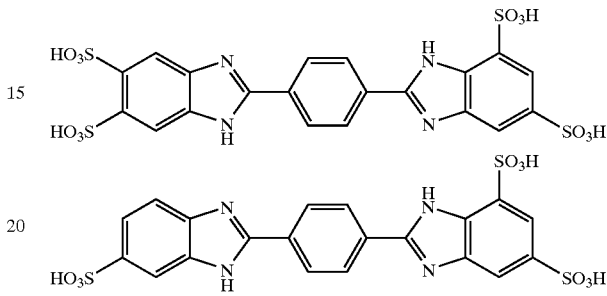

The by-products are safe and cause no discoloration of the phenylene-bis-benzimidazole-tetrasulfonic acid disodium salt.

The preferred reaction time for the process according to the present invention is 11 to 12 hours.

In a preferred embodiment of the process according to the present invention, the phenylene-bis-benzimidazole-tetrasulfonic acid obtained in the reaction or after hydrolysis is, in a first step, dissolved in water and treated with activated carbon, which is then separated off, and where the phenylene-bis-benzimidazole-tetrasulfonic acid disodium salt is precipitated out of the filtrate with sodium chloride and separated off, and, in a second step, is again dissolved in water and sodium hydroxide solution and again treated with activated carbon, which is then again separated off, where pure phenylene-bis-benzimidazole-tetrasulfonic acid disodium salt precipitates out of the filtrate by acidification and is then optionally also purified.

The phenylene-bis-benzimidazole-tetrasulfonic acid obtained in the reaction or after hydrolysis is dissolved in the first step in water in the temperature range from 40 to 80° C., preferably 45 to 55° C.

Preference is given here to preparing a 1 to 30% by weight, preferably 5 to 7% by weight, solution of phenylene-bis-benzimidazole-tetrasulfonic acid.

Activated carbon for the process according to the present invention (first and second step) can be all commercially available types.

To precipitate out the sodium salt, a 1 to 15, preferably 3 to 10, equimolar amount of sodium chloride is generally added.

The phenylene-bis-benzimidazole-tetrasulfonic acid disodium salt obtained in the first step is dissolved in the second step in water in the temperature range from 30 to 80° C., preferably from 45 to 50° C.

Preference is given here to preparing a 5 to 25% by weight, preferably 15 to 20% by weight, solution of phenylene-bis-benzimidazole-tetrasulfonic acid disodium salt.

The phenylene-bis-benzimidazole-tetrasulfonic acid disodium salt obtained in the first step is dissolved and, after treatment with and removal of the activated carbon, precipitated out by acidification to about pH 3. The acidification is preferably carried out using hydrochloric acid. Surprisingly, the disodium salt precipitates out here as well.

The phenylene-bis-benzimidazole-tetrasulfonic acid disodium salt obtained in the second step can be washed again with phosphoric acid in a preferred embodiment.

The process according to the present invention can be carried out, for example, as follows:

Sulfuric acid, terephthalic acid and o-phenylenediamine are initially introduced and the mixture is heated to, for example, 110° C. under a nitrogen atmosphere. Then, over the course of 4 h, chlorosulfonic acid is metered in at a temperature between 110 and 120° C., and then the mixture is further stirred for 12 h. The phenylene-bis-benzimidazole-tetrasulfonic acid obtained after hydrolysis is dissolved at 35–40° C. in water, treated with activated carbon and stirred for about 30 min at the same temperature. The activated carbon is filtered off, and the filtrate is admixed with sodium chloride and slowly cooled to room temperature with stirring over the course of about 2 hours for precipitation. The resulting phenylene-bis-benzimidazole-tetrasulfonic acid disodium salt is then filtered off and after-washed with 5 percent strength sodium chloride solution.

The resulting phenylene-bis-benzimidazole-tetrasulfonic acid disodium salt is again introduced into water and, for dissolution, 45 percent strength sodium hydroxide solution is added to a pH of 5, then activated carbon is added again. The mixture is maintained at 55° C. and stirred for about 2 hours. The activated carbon is separated off and the filtrate is acidified with pure hydrochloric acid to pH 3 to precipitate out the phenylene-bis-benzimidazole-tetrasulfonic acid disodium salt again. The mixture is stirred for about 2 hours and cooled to room temperature. The phenylene-bis-benzimidazole-tetrasulfonic acid disodium salt is separated off in a manner known per se, e.g. by filtration.

The resulting phenylene-bis-benzimidazole-tetrasulfonic acid disodium salt can then also be washed with a 2% by weight aqueous sodium chloride solution which has been adjusted to pH 3 using small amounts of phosphoric acid; drying is then carried out, for example, at 140° C. and 2 mbar.

Use of the process according to the present invention gives a product which is analytically perfect in the trace region, which is best suited for use in cosmetic formulations and does not have the discoloration disadvantages detailed in the introduction. Surprisingly, the presence of problematical trace components is prevented.

Phenylene-bis-benzimidazole-tetrasulfonic acid disodium salt can be used as UV-A filters in cosmetic products.

EXAMPLE 1,703 g of sulfuric acid, 96% are initially introduced and 232 g of terephthalic acid are introduced, then, after the system has been flushed with nitrogen, 302 g of o-phenylenediamine are added in portions, which causes the temperature to increase to 97° C. The temperature is then increased to 110° C. 2,200 g of chlorosulfonic acid are metered in over the course of 4 h, the temperature being maintained between 110–120° C., and, after the metered addition, the mixture is stirred for a further 12 h at said temperature.

The reactor contents are cooled to room temperature, and 4,000 g of water at 5° C. are metered in over the course of 4 h, which causes the temperature to increase to about 47° C., then the mixture is after-stirred for a further 2 h and then filtered, giving 1,200 g of moist phenylene-bis-benzimidazole-tetrasulfonic acid.

This press cake is introduced into 11,000 g of water at 40° C. and dissolved, then 30 g of activated carbon are added. The mixture is stirred for 30 min under nitrogen and then filtered. The filtrate is admixed at 50° C. with 600 g of sodium chloride and stirred for 2 h at this temperature, the temperature being reduced to 25° C. towards the end of the stirring period; and then the mixture is filtered. The resulting product is washed with 2,800 g of 5% by weight sodium chloride solution, giving 1,362 g of phenylene-bis-benzimidazole-tetrasulfonic acid disodium salt.

The resulting phenylene-bis-benzimidazole-tetrasulfonic acid disodium salt is introduced into 4,500 g of water at 50° C. and suspended (pH 2.4); then, at 50° C., 168 g of 45 percent strength sodium hydroxide solution is added to adjust the pH to 5 and to dissolve the product, then 30 g of activated carbon are added, the mixture is heated to 55° C. and after-stirred for 2 h and filtered, the filtrate is treated with 162 g of pure hydrochloric acid, then the temperature is maintained at 50° C. and a pH of 3 is adjusted, the mixture is stirred for 2 h under nitrogen and cooled to 25° C.; the mixture is then filtered and the filter cake is then washed with 4,000 g of 2 percent strength sodium chloride solution which has been adjusted to pH 3 using a small amount of phosphoric acid, giving 1,155 g of the thus purified phenylene-bis-benzimidazole-tetrasulfonic acid disodium salt.

The thus purified phenylene-bis-benzimidazole-tetrasulfonic acid disodium salt is then dried for 10 h at 140° C. and 2 mbar, giving 700 g of end-product (residual moisture 2%). The resulting phenylene-bis-benzimidazole-tetrasulfonic acid disodium salt has a purity of 98% by weight and comprises as by-products merely

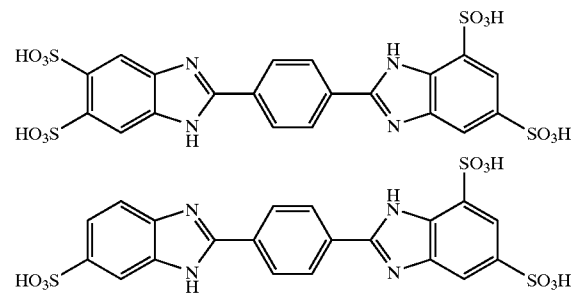

The by-products are safe and cause no discoloration of the phenylene-bis-benzimidazole-tetrasulfonic acid disodium salt.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of phenylene-bis-benzimidazole-tetrasulfonic acid di-sodium salt substantially free of discoloration causing by-products comprising:
    (a) reacting o-phenylene-diamine with terephthalic acid and chlorosulfonic acid in the presence of strong acids, wherein the reaction time is 10 to 15 hours,
    (b) dissolving the phenylene-bis-benzimidazole-tetrasulfonic acid obtained in step (a) in water and treating the solution with activated carbon, which activated carbon is then separated off, followed by precipitating out phenylene-bis-benzimidazole-tetrasulfonic acid disodium salt by adding sodium chloride and separating off the water, and (c) dissolving the phenylene-bis-benzimidazole-tetrasulfonic acid disodium salt precipitate of step (b) in water and sodium hydroxide solution, followed by treating the resulting solution with activated carbon, which activated carbon is then separated off, (d) acidifying the solution obtained in step (c) to precipitate out phenylene-bis-benzimidazole-tetrasulfonic acid disodium salt substantially free of by-products which would cause discoloration of phenylene-bis-benzimidazole-tetrasulfonic acid disodium salt, and (e) optionally further purifying the product of step (d).

2. The process according to claim 1, wherein the phenylene-bis-benzimidazole-tetrasulfonic acid obtained in the reaction is dissolved in the first step in water in the temperature range from 40 to 80° C.

3. The process according to claim 1, wherein the phenylene-bis-benzimidazole-tetrasulfonic acid disodium salt obtained in the first step is dissolved in the second step in water in the temperature range from 30 to 80° C.

4. The process according to claim 1, wherein the phenylene-bis-benzimidazole-tetrasulfonic acid disodium salt obtained in the first step is dissolved an the second step in water and, after treatment with and removal of the activated carbon, is precipitated out by acidification to about pH 3.

5. The process according to claim 1, wherein the acidification in the second step is carried out with hydrochloric acid.

6. The process according to claim 1, wherein the phenylene-bis-benzimidazole-tetrasulfonic acid disodium salt obtained in the second step is washed with phosphoric acid.

7. The process as in claim 1, wherein step (a) is carried out at a temperature of from 110° C. to 120° C.

* * * * *